United States Patent
Chiang (10) Patent No.: US 12,053,243 B2
(45) Date of Patent: Aug. 6, 2024

(54) POSITIONING AND NAVIGATION SYSTEM FOR SURGERY AND OPERATING METHOD THEREOF

(71) Applicant: Orion Biotech Inc., Taipei (TW)

(72) Inventor: Ming-Fu Chiang, Taipei (TW)

(73) Assignee: NEUCEN BIOMED CO., LTD., Taipei (TW)

( * ) Notice: Subject to any disclaimer, the term of this patent is extended or adjusted under 35 U.S.C. 154(b) by 803 days.

(21) Appl. No.: 16/565,278

(22) Filed: Sep. 9, 2019

(65) Prior Publication Data

US 2021/0000545 A1 Jan. 7, 2021

(30) Foreign Application Priority Data

Jul. 3, 2019 (CN) .......................... 201910594416.3

(51) Int. Cl.
*A61B 34/20* (2016.01)
*G06T 19/00* (2011.01)
*A61B 90/00* (2016.01)
*A61B 90/50* (2016.01)

(52) U.S. Cl.
CPC ............ *A61B 34/20* (2016.02); *G06T 19/006* (2013.01); *A61B 2034/2048* (2016.02); *A61B 2034/2051* (2016.02); *A61B 2034/2055* (2016.02); *A61B 2034/2065* (2016.02); *A61B 2090/365* (2016.02); *A61B 2090/367* (2016.02); *A61B 2090/368* (2016.02); *A61B 2090/502* (2016.02); *G06T 2210/41* (2013.01)

(58) Field of Classification Search
None
See application file for complete search history.

(56) References Cited

U.S. PATENT DOCUMENTS

| | | | | |
|---|---|---|---|---|
| 5,704,355 | A | * | 1/1998 | Bridges ................ A61B 5/0507 600/407 |
| 9,892,564 | B1 | * | 2/2018 | Cvetko .................. G16H 20/40 |
| 2014/0188440 | A1 | * | 7/2014 | Donhowe .............. A61B 10/04 703/1 |
| 2018/0078316 | A1 | * | 3/2018 | Schaewe .............. A61B 5/0035 |
| 2018/0140362 | A1 | * | 5/2018 | Calì ....................... A61B 34/20 |

FOREIGN PATENT DOCUMENTS

| | | |
|---|---|---|
| CN | 1536975 A | 10/2004 |
| CN | 1681448 A | 10/2005 |
| CN | 101252870 A | 8/2008 |

(Continued)

*Primary Examiner* — Boniface N Nganga
(74) *Attorney, Agent, or Firm* — Cheng-Ju Chiang (57) ABSTRACT

The present invention discloses a positioning and navigation system for surgery, comprising a wearable device and a surgical instrument connected to the wearable device. The wearable device comprises at least one processor, at least one millimeter-wave positioning module connected to the at least one processor, and a first display module connected to the at least one processor. The invention may detect the image information of the surgical site of the patient through at least one millimeter-wave positioning module, and display the image information on the first display module. Thereby, the invention assists the surgical instrument or doctor who wears the wearable device positioning and navigation during the surgery procedure.

17 Claims, 6 Drawing Sheets

(56) References Cited

FOREIGN PATENT DOCUMENTS

| | | | |
|---|---|---|---|
| CN | 105395252 | A | 3/2016 |
| CN | 107402378 | A | 11/2017 |
| CN | 208031283 | U | 11/2018 |
| CN | 109674532 | A | 4/2019 |
| CN | 109785374 | A | 5/2019 |
| TW | 201727439 | A | 8/2017 |
| WO | 2018/200553 | A1 | 11/2018 |
| WO | 2019/100212 | A1 | 5/2019 |

* cited by examiner

POSITIONING AND NAVIGATION SYSTEM FOR SURGERY AND OPERATING METHOD THEREOF

TECHNICAL FIELD

The present invention relates to a positioning and navigation system and operating method thereof, particularly, a positioning and navigation system for surgery and operating method thereof.

BACKGROUND OF RELATED ARTS

Navigation and positioning systems generally comprise mechanical, optical and electromagnetic tracking and positioning modes. However, at present, these three navigation modes have their disadvantages that cannot be neglected.

Firstly, the mechanical tracking system uses a robotic manipulator as a tracker, which has great accuracy and stability of positioning. However, the tracking range of the system is limited by the manipulator mechanism, so that the freedom of the mechanical tracking system is poor, and the accessible rang is small.

On the other hand, the optical tracking system, which is commonly used nowadays, is mostly tracked by an infrared sensor. The mechanism of the optical tracking system is to use infrared light source of a sensing camera for tracking; specifically, the outer ring of the sensing camera is an infrared transmitter, and the inner ring is an infrared receiver. However, although the accuracy and stability of infrared light source sensing are adequate, it is easy to be masked. Thereby, the optical tracking system is mostly used for external positioning and related information extraction.

Electromagnetic tracking system uses the mechanism of magnetic field induction to retrieve spatial information. Without the restriction of the line-of-sight, the electromagnetic tracking system does not be affected during the operation process by the shield. In recent years, due to the development of fabrication process and related technology, the miniature sensor can be used in the tracker entering into the human body. However, the accuracy and stability of magnetic field are low, and it will be disturbed by external electromagnetic waves, which makes it difficult to position for large area.

Lastly, the main positioning method in development is to judge spatial information through the image processing, and then position and navigate by said spatial information through the image processing. One of abovementioned method is to use two or more different CCD cameras with known positions, and then reconstructing the captured image to achieve stereo vision effect for positioning. The other one is to use only a set of CCD camera, and then modeling and overlapping to achieve indirect positioning. Both of the above methods are achieved by image processing, they also provide the ability of tissue identification. However, this kind of method is mainly based on the post-processing of the photographed image, not directly positioning, so the accuracy of positioning still needs to be greatly improved. Furthermore, this kind of method requires a lot of image processing and calculation, it is difficult to achieve large area and real-time positioning.

In regards with the aforementioned method, the most common navigation and positioning method is infrared sensing device. In the process of positioning through the infrared light, it is necessary to add a navigation marker on the surgical instrument or related device, and then position the navigation marker to know the relative position. However, the navigation marker has a certain volume, so users need to avoid shading to the infrared light path by the navigation marker when operating. Therefore, the infrared sensing device is also inconvenience to use.

SUMMARY

To resolve the drawbacks of the abovementioned prior arts, the present invention discloses a positioning and navigation system for surgery, comprising: a wearable device including at least one processor, at least one millimeter-wave positioning module coupled to the at least one processor, and a first display module coupled to the at least one processor; and a surgical instrument coupled to the wearable device.

Additionally, the present invention further discloses another positioning and navigation system for surgery, comprising: a wearable device including at least one processor, an auxiliary positioning module to detect a surgical site of a patient, the auxiliary positioning module comprises at least one sensing unit, and a first display module coupled to the at least one processor; at least one millimeter-wave positioning module coupled to the at least one processor; and a surgical instrument coupled to the wearable device and the at least one millimeter-wave positioning module. The auxiliary positioning module is further configured to detect a position of the surgical instrument.

Moreover, the present invention discloses an operation method of the positioning and navigation system for surgery, comprising: (A) detecting a surgical site of a patient to obtain a local three-dimensional feature points image by a wearable display device, the wearable display device includes at least one millimeter-wave positioning module, an auxiliary positioning module and a display module; (B) overlapping a three-dimensional virtual image with the local three-dimensional feature points image to form an overlapped three-dimensional image to display on the first display module; and (C) performing a surgical procedure for the patient according to the overlapped three-dimensional image; and the wearable display device is continuously calibrating and updating the overlapped three-dimensional image in real time through at least one sensing information detected by the auxiliary positioning module or the millimeter wave positioning module. Moreover, before the abovementioned step (A), the method further comprises the following steps: (a) scanning the surgical site of the patient to obtain at least one first two-dimensional image by an external device; and (b) reconstructing the at least one two-dimensional image to form the three-dimensional virtual image by the first image processing module.

Embodiments of the invention are illustrated by way of example, and not by way of limitation, in the figures of the accompanying drawings in which like reference numerals refer to similar elements.

DETAILED DESCRIPTION OF THE INVENTION

In order to understand the technical features and practical efficacy of the present invention and to implement it in accordance with the contents of the specification, hereinafter, preferred embodiments of the present invention will be described in detail with reference to the accompanying drawings.

The invention provides a positioning and navigation system for surgery and its operation method. The millimeter wave positioning module in the system can detect the surgical site of a patient, construct a two-dimensional or three-dimensional image of the surgical site and display it by the display module. Thereby, the system may assist the positioning and navigation of the surgical instrument or executor of surgical operation (such as doctor) in order to improve the accuracy and efficiency of the surgical process. Specifically, the types of surgical operations applicable in the following embodiments may include neurosurgery, orthopaedic surgery, endoscopic surgery, etc., and the present invention should not be limited thereto.

Figure 1:
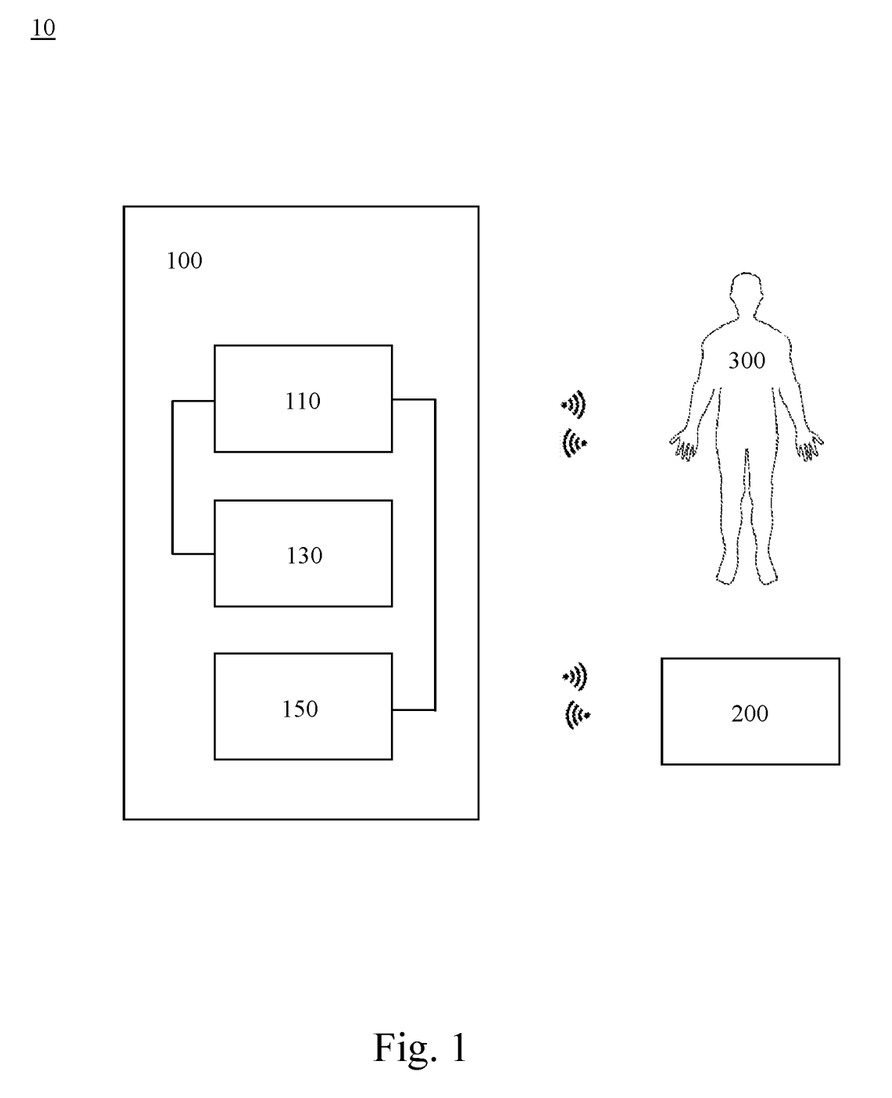
FIG. 1 illustrates a schematic diagram of the positioning and navigation system of the first embodiment of the present invention.
Figure 2:
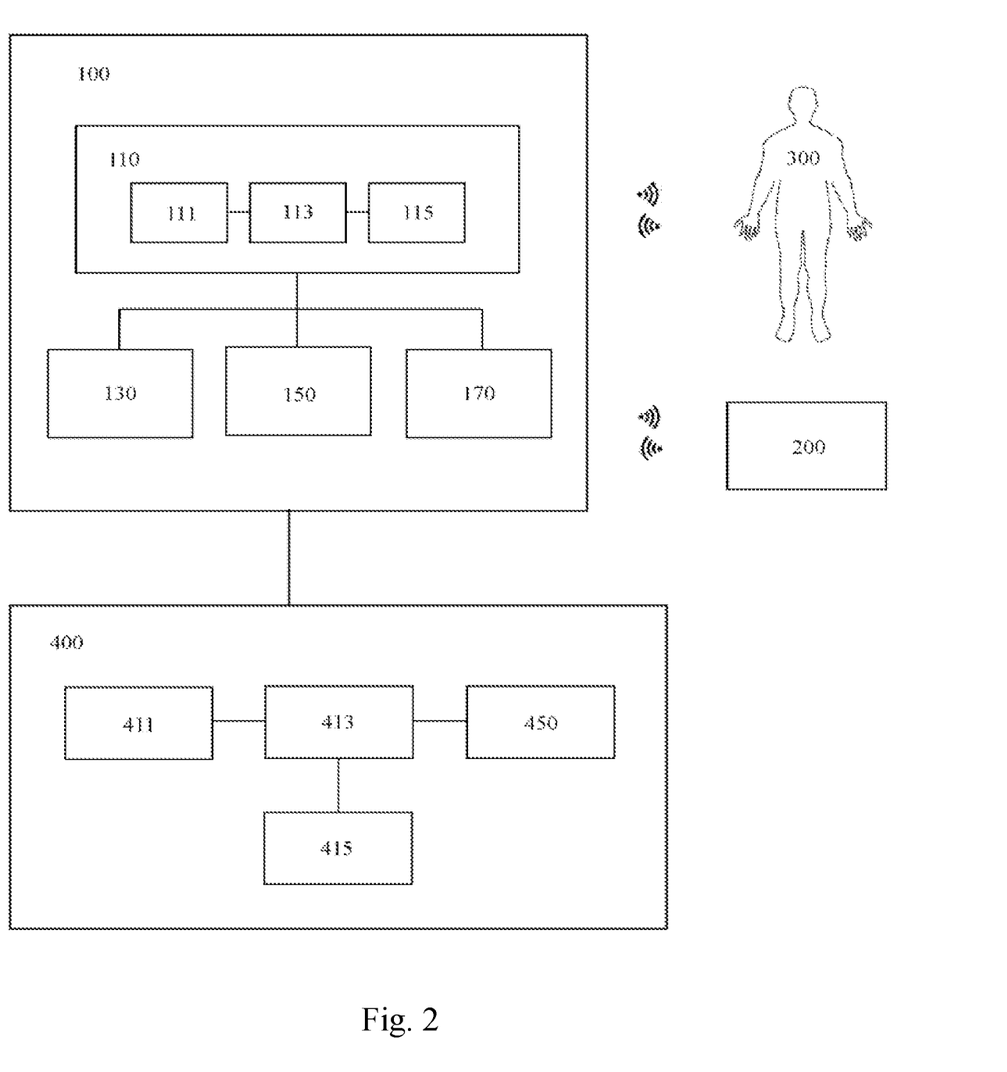
FIG. 2 illustrates a detailed schematic diagram of the positioning and navigation system of the first embodiment of the present invention.

First of all, please refer to the FIGS. 1 and 2 simultaneously, FIG. 1 illustrates a schematic diagram of the positioning and navigation system of the first embodiment of the present invention, and FIG. 2 illustrates a detailed schematic diagram of the positioning and navigation system of the first embodiment of the present invention. As shown in FIG. 1, the positioning and navigation system 10 for surgery of the present embodiment includes a wearable device 100 and a surgical instrument (device) 200 wired connecting or wirelessly connected with the wearable device 100. The wearable device 100 may be a wearable bracelet, arm band, wrist band, finger ring, headband or eye mask, etc., in this embodiment the wearable device is wearable glasses. Furthermore, the wearable device 100 includes at least one processor 110, at least one millimeter-wave positioning module 130 connected to the at least one processor 110, and a first display module 150 connected to the at least one processor 110. The at least one processor 110 can calculate and process the information received by at least one millimeter wave positioning module 130, and output the results to display by the first display module 150 to assist the surgical instrument 200 or the executor of surgical operation (such as a doctor) wearing the wearable device to position and navigate for the surgical site of the patient 300.

The following will further interpret the positioning and navigation system of the first embodiment. Please refer to FIG. 2 and in conjunction with FIG. 1, the at least one processor 110 in this embodiment includes a first information transceiver module 111 and a first image processing module 113 connected to the first information transceiver module 111. The first transceiver module 111 can receive at least one image information scanned by an external device (not shown). Specifically, the at least one image information can be the image information (e.g. two-dimensional image information) constructed by computed tomography (CT), magnetic resonance imaging (MM), functional magnetic resonance imaging (FMRI), diffusion tensor imaging (DTI) or their combination for the surgical site of the patient. The first image processing module 113 can reconstruct the two-dimensional image information to form a three-dimensional virtual image.

Figure 5:
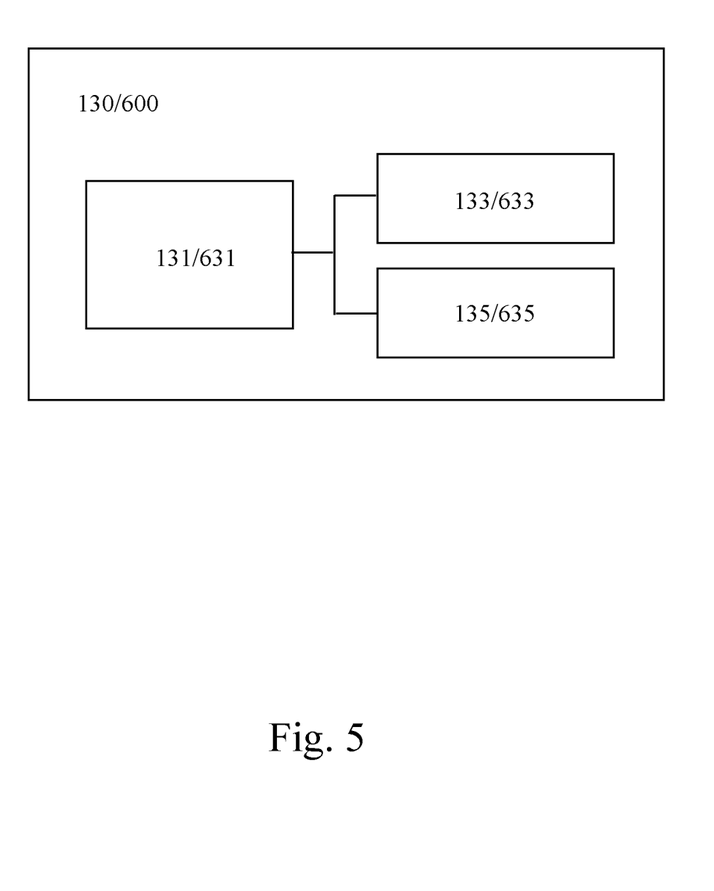
FIG. 5 illustrates a millimeter wave positioning module according to one embodiment of the present invention.

The millimeter wave positioning module 130 further includes a signal processing unit 131, a signal transmitting unit 133 and a signal receiving unit 135 (referring to FIG. 5). The signal transmitting unit 133 may send a millimeter wave signal with a frequency range of 24-300 GHz, or a frequency range of 24-300 GHz millimeter wave signal combined with a frequency range of 3-30 GHz super high frequency (SHF) signal for the surgical site of the patient 300. For example, the signal may be a millimeter-wave signal with a frequency range of 24.25-27.5 GHz, a millimeter-wave signal with a frequency range of 31.8-33.4 GHz, a millimeter-wave signal with a frequency range of 37-40.5 GHz, a millimeter-wave signal with a frequency range of 40.5-42.5 GHz, a millimeter-wave signal with a frequency range of 45.5-50.2 GHz, a millimeter-wave signal with a frequency range of 50.4-52.6 GHz, a millimeter-wave signal with a frequency range of 66-76 GHz, or a millimeter-wave signal with a frequency range of 81-86 GHz, and the invention should not be limited to the above frequency range. The signal receiving unit 135 can receive the reflected millimeter wave signals as detecting the surgical site of the patient 300. Finally, the signal processing unit 131 instantly identifies the tissue site information and depth information of the surgical site, and constructs a three-dimensional feature points image of the surgical site of the patient 300 through the relevant information (such as the tissue site information and depth information of the patient's surgical site) obtained by the signal receiving unit 135. It should be noted that the three-dimensional feature points image may be a global three-dimensional feature points image of the surgical site or a local three-dimensional feature points image of the surgical site.

Subsequently, the first image processing module 113 of the at least one processor 110 receives the global three-dimensional feature points image or the local three-dimensional feature points image constructed by the millimeter-wave positioning module 130 in real time. Then, the first image processing module 113 is configured to overlap the three-dimensional virtual image with the three-dimensional feature points image (including the global three-dimensional feature points image or the local three-dimensional feature points image) to form an overlapped three-dimensional image of the surgical site of the patient 300. The overlapped three-dimensional image is displayed by the first display module 150. Therefore, it can simultaneously provide the executing doctor with the surgical site and images information during the operation, and more accurately acquire (aim at) the position of the surgical knife to reduce the surgical error. Furthermore, the processor 110 may also include a surgical navigation module 115 connected to the first image processing module 113. The user (e.g. a doctor) may input a surgical navigation information from the outside to the surgical navigation module 115 based on the three-dimensional overlapped image, or the surgical navigation module 115 may calculate the surgical navigation information based on the overlapped three-dimensional image to display by the first display module 150 to enable the doctor to know the surgical path immediately during the surgical procedure according to the navigation information so as to avoid dangerous areas.

It should be noted that the first display module 150 is not only a general display device such as a projector, a screen or display panel, but also a virtual reality (VR), an augmented reality (AR) or a mixed reality (MR) display device to display virtual reality images, enhanced reality images or mixed reality images.

In addition, the signal processing unit 131 can also calculate the relative distance between the millimeter wave positioning module 130 (or the wearable device 100) and the surgical site of the patient 300 based on the time difference from millimeter wave transmitting signal of the signal transmitting unit 133 to millimeter wave receiving signal of the signal receiving unit 135, and further calculate (determine) the moving position, acceleration, angular velocity, rotation angle or their combination of the wearable device 100 relative to the surgical site of the patient 300 to adjust and calibrate the three-dimensional overlapped image on the first display module 150. When the surgical executor wearing the wearable device 100 moves or rotates the wearing part (the head), the three-dimensional overlapped image on the first display module 150 can be continuously updated with the distance or angle of the movement or rotation of the wearable device 100.

Finally, the surgical instrument (device) 200 connected with the wearable device 100 can receive the three-dimensional overlapped image and/or the surgical navigation information mentioned above to assist the operator (such as a doctor) to perform the surgical procedure accurately for the surgical site of the patient 300, or directly perform the operation through the surgical instrument 200 for the surgical site of the patient 300 according to the surgical navigation information.

In the first embodiment, the wearable device 100 further comprises an auxiliary positioning module 170 connected to the at least one processor 110. The auxiliary positioning module 170 comprises at least one sensing unit, at least one camera unit or the combination thereof to obtain at least one second sensing information. The at least one sensing unit includes a gyroscope, a magnetometer, an accelerometer, an infrared sensor, a magnetometer, a microwave sensor or the combination thereof. The sensing unit may also be a nine-axis motion sensor or an inertial measurement unit (IMU). The nine-axis motion sensor consists of three-axis gyroscope, three-axis magnetometer and three-axis accelerometer. The inertial measurement unit consists of three accelerometers and three gyroscopes. The purpose of the above both is to detect the angle, position, displacement, rotation and speed of the wearable device 100 relative to the surgical site of the patient 300 or the surgical device 200. The sensor unit can detect the initial position, termination position, relative position, displacement, triaxial rotation matrix, angle (direction angle or pitch angle), velocity and acceleration of the wearable device relative to the surgical site of the patient. The at least one camera unit may be a camera, a video camera or its combination, which purpose is to capture the image of the surgical site of the patient 300 and to calculate the relative distance between the surgical site of the patient 300 or the surgical device 200 and the wearable device 100 through the image.

Through at least one second sensing information generated by the aforementioned auxiliary positioning module 170, the processor 110 can be further known that the moving position, acceleration, angular velocity, rotation angle or their combination of the wearable device 100 relative to the surgical site of the patient 300 or the surgical device 200 can be configured to judge the movement track of the wearable device 100 when the doctor performs the surgery procedure. Thereby, the processor 110 may continuously update the three-dimensional overlapped images on the first display mode 150 in real time.

In addition, the positioning and navigation system of the first embodiment further includes an external server 400 wired connection or wirelessly connected to the wearable device 100. The external server 400 includes a second information transceiver module 411, a second image processing module 413 connected to the at least one millimeter-wave positioning module 130 and the second information transceiver module 411, a second image processing module 413 connected to the second image processing module 413, a second display module 450 connected to the second image processing module 413, and a surgical navigation module 415 connected with the second image processing module 413. Similar with the first image transceiver module 111, the second image transceiver module 411 can receive at least one image information (such as two-dimensional image information) scanned by an external device (such as CT, MRI, FMRI or DTI), and the second image processing module 413 can also reconstruct the two-dimensional image information to form a three-dimensional virtual image. Subsequently, the second image processing module 413 can receive the global three-dimensional feature points image or the local three-dimensional feature points image constructed by the millimeter wave positioning module 130 in real time. At the same time, the second image processing module 413 superimposes the three-dimensional virtual image and the three-dimensional feature points image (including the global three-dimensional feature points image and/or the local three-dimensional feature points image) to form a three-dimensional overlapping image of the surgical site of the patient 300 and display the image on the first display module 150 or the second display module 450 described above. Finally, the surgical navigation module 415 is similar to the surgical navigation module 115 mentioned above, and can input a surgical navigation information from the external to the surgical navigation module 415 based on the three-dimensional overlapped image, or the surgical navigation module 415 can calculate the surgical navigation information based on the three-dimensional overlapped image and present it on the first display module 150 or the second display module 450.

From the above description, it can be seen that the external server 400 in this embodiment can perform the function of the processor 110 in the wearable device 100. In other some embodiments, the processor 110 in the wearable device 100 can be removed and the related information detected by the millimeter wave positioning module 130 or the auxiliary positioning module 170 can be output to the external server 400 for processing. After processing, the image is then transmitted to the display module 150 of the wearable device 100 to display the corresponding image.

Figure 3:
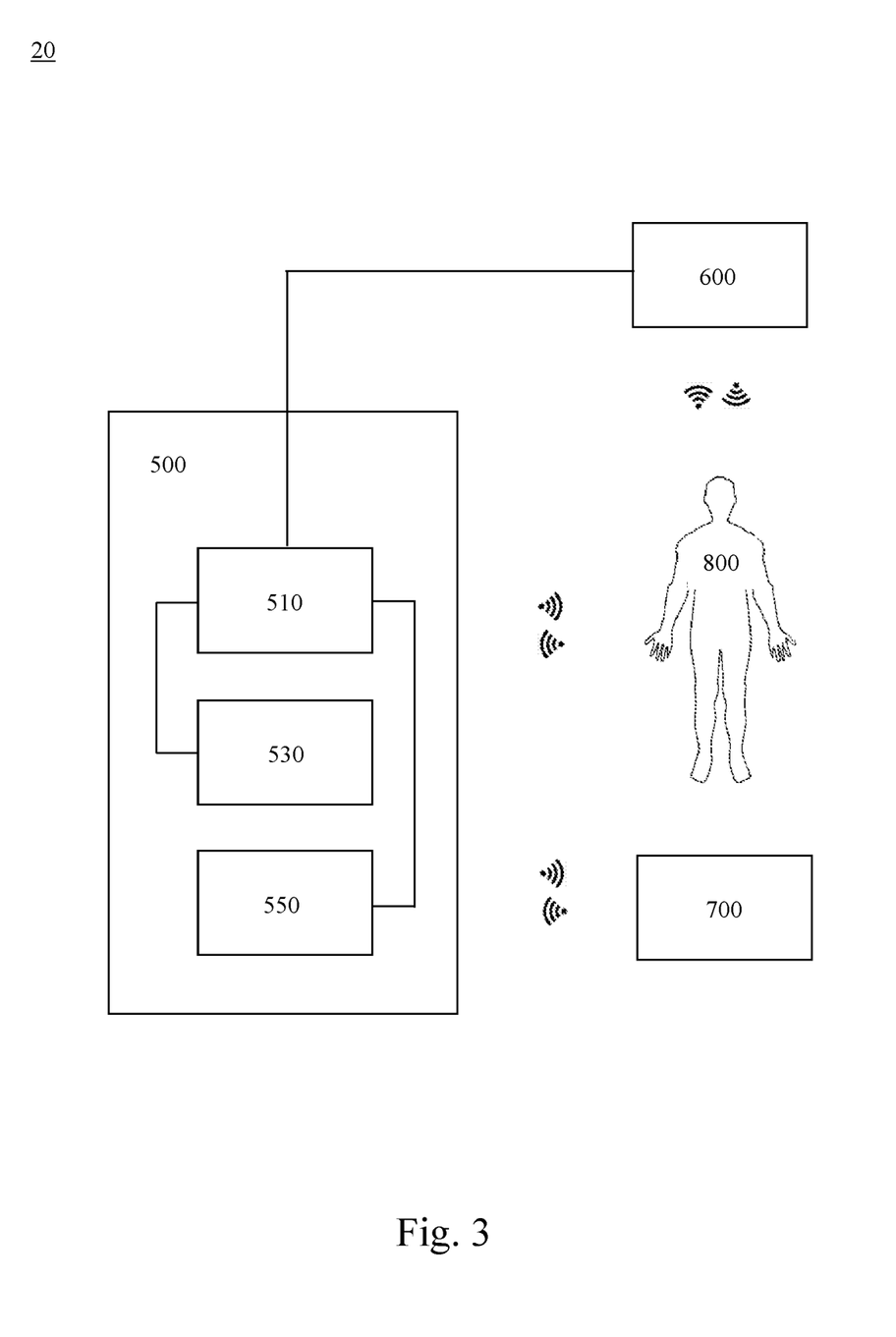
FIG. 3 illustrates a schematic diagram of the positioning and navigation system of the second embodiment of the present invention.
Figure 4:
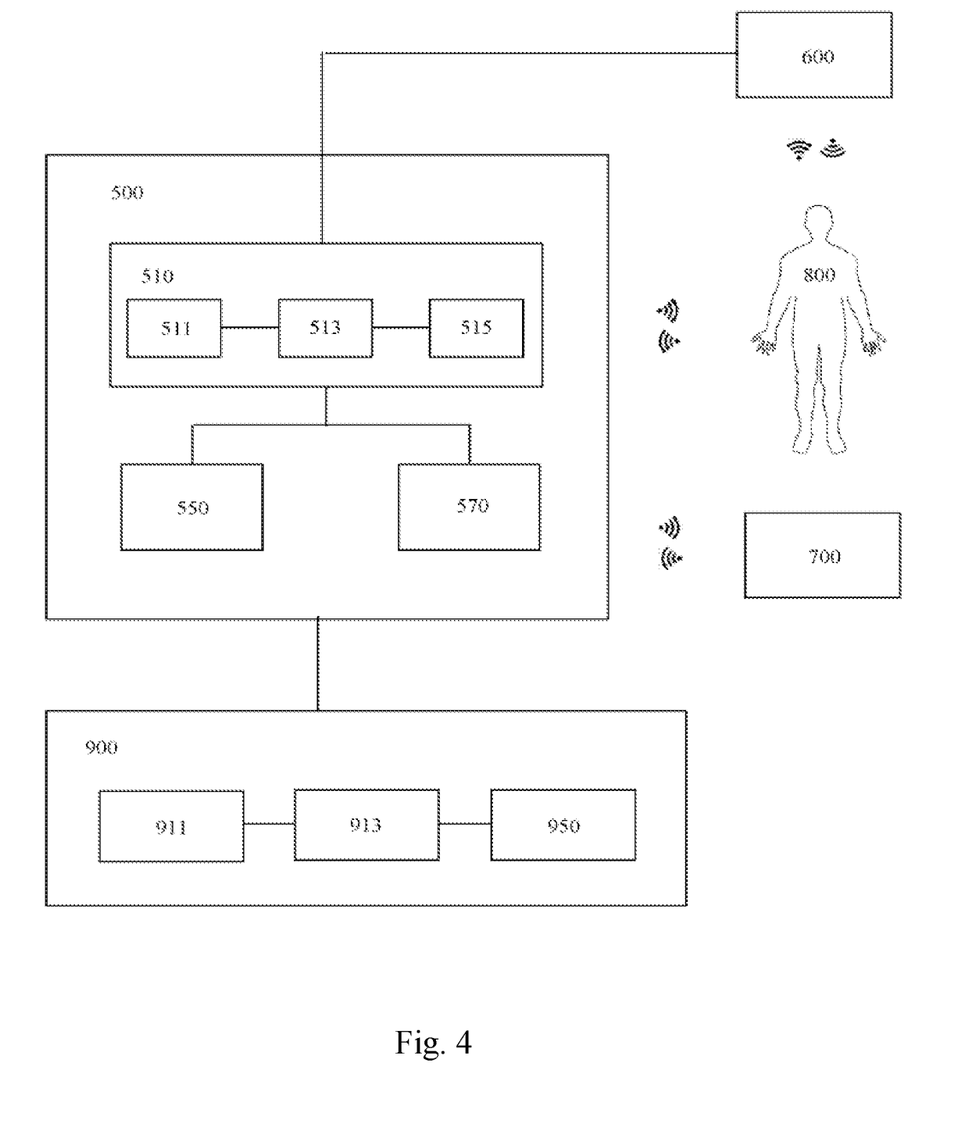
FIG. 4 shows a detailed schematic diagram of the positioning and navigation system of the second embodiment of the present invention.

On the other hand, referring to FIG. 3 and FIG. 4, FIG. 3 illustrates a schematic diagram of the positioning and navigation system of the second embodiment of the present invention, and FIG. 4 shows a detailed schematic diagram of the positioning and navigation system of the second embodiment of the present invention. As shown in FIG. 3, the positioning and navigation system 20 for surgery of the present embodiment includes a wearable device 500, at least one millimeter-wave positioning module 600 wired connection or wirelessly connected to the wearable device 500, and a surgical device 700 wired connection or wirelessly connected to the wearable device 500. The wearable device 500 may be a wearable bracelet, arm band, wrist band, finger ring, headband or eye mask, etc. In this embodiment, the wearable device 500 is wearable glasses. Furthermore, the wearable device 500 includes at least one processor 510, an auxiliary positioning module 570 connected to the at least one processor 510 and a first display module 550 connected to the at least one processor 510. The auxiliary positioning module 570 includes at least one sensing unit (such as infrared sensor, camera) configured to detect the surgical site of a patient 800 or the location of surgical device. The at least one processor 510 can calculate and process the information received by the auxiliary positioning module 570 and the at least one millimeter wave positioning module 600, and output the processed results to the first display module 550 to assist the surgical device 700 or the operator (such as a doctor) wearing the wearable device 500 for positioning and navigation. The difference between the positioning and navigation system of the second embodiment and the first embodiment is that the image information formed by a wearable device having a photo sensing unit combined with the at least one millimeter-wave positioning module is used for positioning and navigation in the second embodiment.

The following will further explain the positioning and navigation system of the second embodiment. Referring to FIG. 4 and in conjunction with FIG. 3, the at least one processor 510 in this embodiment further includes a first information transceiver module 511 and a first image processing module 513 connected to the first information transceiver module 511. The first information transceiver module 511 can receive at least one image information scanned by an external device. Specifically, the at least one image information can be computed tomography (CT), magnetic resonance imaging (MRI), functional magnetic resonance imaging (FMRI), diffusion tensor imaging (DTI) image information (such as two-dimensional image information) for the surgical site of the patient 800, or their combination. The first image processing module 513 can reconstruct the two-dimensional image information to form a three-dimensional virtual image.

The auxiliary positioning module 570 of the wearable device 500 is connected with the at least one processor 510 to detect the surgical site of the patient 800. The auxiliary positioning module 570 includes at least one sensing unit, at least one camera unit or the combination thereof to obtain at least one sensing information and at least one two-dimensional image. The at least one sensing unit includes a gyroscope, a magnetometer, an accelerometer, an infrared sensor, a magnetometer, a microwave sensor or the combination thereof. The sensing unit may also be a nine-axis motion sensor or an inertial measurement unit (IMU). The nine-axis motion sensor consists of three-axis gyroscope, three-axis magnetometer and three-axis accelerometer. The inertial measurement unit consists of three accelerometers and three gyroscopes. The purpose of both above is to detect the angle, position, displacement, rotation and speed of the wearable device 500 relative to the surgical site of the patient 800 or the surgical device 700. The sensing unit can detect the initial position, termination position, relative position, displacement, triaxial rotation matrix, angle (direction angle or pitch angle), velocity and acceleration of the wearable device 500 relative to the surgical site of the patient. The at least one camera unit may be a camera, a video camera or the combination thereof, and the purpose of the camera unit or the infrared sensor is to capture at least one two-dimensional image of the surgical site of the patient 800.

The millimeter wave positioning module 600 further includes a signal processing unit 631, a signal transmitting unit 633 and a signal receiving unit 635 (referring to FIG. 5). The signal transmitting unit 633 can emit a millimeter wave signal with a frequency range of 24-300 GHz, or a 24-300 GHz millimeter wave signal combined with a 3-30 GHz super high frequency (SHF), for the surgical site of the patient 800. For example, it may be a millimeter-wave signal with a frequency range of 24.25-27.5 GHz, a millimeter-wave signal with a frequency range of 31.8-33.4 GHz, a millimeter-wave signal with a frequency range of 37-40.5 GHz, a millimeter-wave signal with a frequency range of 40.5-42.5 GHz, a millimeter-wave signal with a frequency range of 45.5-50.2 GHz, a millimeter-wave signal with a frequency range of 50.4-52.6 GHz, and a millimeter-wave signal with a frequency 66-76 GHz, a millimeter-wave signal with a frequency range of 81-86 GHz, and the invention should not be limited to the above ranges. The signal receiving unit 635 can receive the millimeter wave signal reflected by detecting the surgical site, and instantly identify the tissue site information and/or depth information of the surgical site through the signal processing unit 631.

Subsequently, the first image processing module 513 of the at least one processor 510 receives the tissue site information and/or depth information obtained by the millimeter wave positioning module 600 and at least one two-dimensional image obtained by the auxiliary positioning module 570 to construct a three-dimensional feature points image of the surgical site of the patient 800. It should be noted that the three-dimensional feature points image can be a global three-dimensional feature points image in the surgical site, or a local three-dimensional feature points image in the surgical site. At the same time, the first image processing module 513 superposes the three-dimensional virtual image and the three-dimensional feature points image (including the global three-dimensional feature points image and/or the local three-dimensional feature points image) to form a three-dimensional superposed image of the surgical site of the patient 800, and displays the superposed three-dimensional image on the first display module 550, providing the doctor with surgical site and image information during the operation for more precisely locking at the position of surgical knife to reduce surgical errors. Furthermore, the processor 510 can also include a surgical navigation module 515 connected to the image processing module 513. The user (such as a doctor) can input a surgical navigation information from the external to the surgical navigation module 515 based on the three-dimensional overlapped image, or the surgical navigation module 515 can calculate the surgical navigation information based on the three-dimensional overlapped image. The first display module 550 allows the doctor to know the surgical path immediately during the operation based on the navigation information to avoid dangerous areas.

It should be noted that the first display module 550 is not only a general display device such as a projector, a screen or display panel, but also a virtual reality (VR), an augmented reality (AR) or a mixed reality (MR) display device to display virtual reality images, augmented reality images or mixed reality images.

In addition, the auxiliary positioning module 570 generates at least one sensing information, which further reveals the moving position, acceleration, angular velocity, rotation angle or their combination of the wearable device with respect to the surgical site of the patient 800 or the surgical device 700, thereby judging the trajectory of the wearable device 500 when the doctor performs the operation, to continuously update the three-dimensional overlapped image on the first display module 550 in real time. When the operator wearing with the wearable device 500 moves or rotates the wearing part (in this case, the head), the three-dimensional overlapped image on the first display module 550 can be continuously updated with the moving distance or rotating angle of the wearable device 500.

Finally, the surgical device 700 connected with the wearable device 500 can receive the overlapped three-dimensional image and/or navigation information mentioned above to assist the operator (e.g. a doctor) to perform the operation accurately on the surgical site of the patient 800, or directly perform the operation for the surgical site of the patient 800 according to the navigation information of the operation through the surgical device 700.

In addition, the positioning and navigation system of the second embodiment includes an external server 900 wired connection or wirelessly connected with the wearable device 500. The external server 900 comprises a second information transceiver module 911, a second image processing module connected to the at least one millimeter-wave positioning module 600, the auxiliary positioning module 570 and the second information transceiver module 911, a second display module 950 connected to the second image processing module 913, and a second surgical navigation module (not shown) connected to the second image processing module 913. Similarly with the first information transceiver 511, the second information transceiver module 911 can receive at least one image information (such as two-dimensional image information) scanned by an external device (such as CT, MRI, FMRI or DTI), and the second image processing module 913 can also reconstruct the two-dimensional image information to form a three-dimensional virtual image. Subsequently, the second image processing module 913 can also receive the tissue site information and/or depth information obtained by the millimeter wave positioning module 600 and at least one two-dimensional image obtained by the auxiliary positioning module 570 to construct a three-dimensional feature points image of the surgical site of the patient 800. At the same time, the second image processing module 913 superposes the three-dimensional virtual image with the three-dimensional feature points image (including global three-dimensional feature points image and/or the local three-dimensional feature points image) to form a superposed three-dimensional image of 800 surgical sites of patients, and displays the superposed three-dimensional image on the first display module 550 or the second display module 950 mentioned above. Finally, the second surgical navigation module is similar to the first surgical navigation module mentioned above, which can input a surgical navigation information from the outside to the surgical navigation module based on the superposed three-dimensional image, or the surgical navigation module can calculate the surgical navigation information based on the superposed three-dimensional image and display it on the first display module 550 or the second display module 950.

Figure 6:
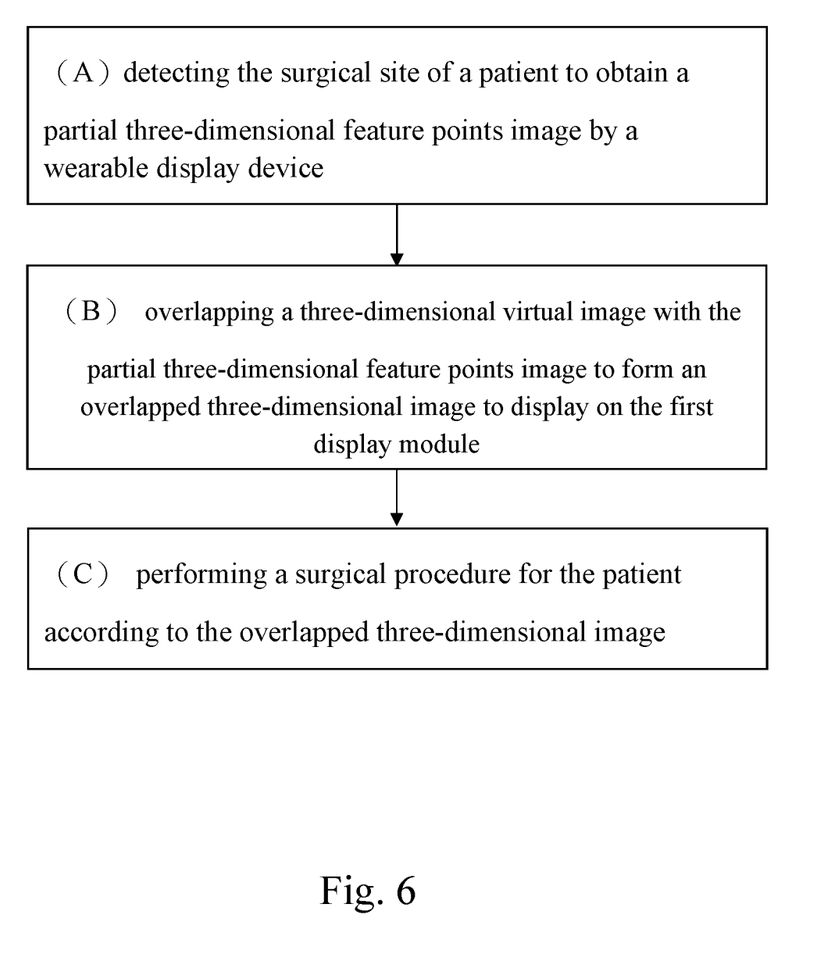
FIG. 6 illustrates a flow chart of the operation method of the positioning and navigation system for surgery in a preferred embodiment of the present invention.

Finally, referring to FIG. 6, it illustrates a flow chart of the operation method of the positioning and navigation system for surgery in a preferred embodiment of the present invention. As shown in FIG. 6, the operation method of the positioning and navigation system for surgery in the present embodiment includes the following steps: (A) detecting the surgical site of a patient to obtain a local three-dimensional feature points image by a wearable display device, in which the wearable display device comprises at least one millimeter wave positioning module, an auxiliary positioning module and a display module; (B) overlapping a three-dimensional virtual image with the local three-dimensional feature points image to form an overlapped three-dimensional image to display on the first display module; and (C) performing a surgical procedure for the patient according to the overlapped three-dimensional image; the wearable display device can correct and update the overlapped three-dimensional image in real time through at least one sensing information detected by the auxiliary positioning module or the millimeter wave positioning module.

Moreover, before the abovementioned step (A), the method further comprises the following steps: (a) scanning the surgical site of the patient to obtain at least one first two-dimensional image by an external device; and (b) reconstructing the at least one two-dimensional image to form the three-dimensional virtual image by the first image processing module.

The advantages of the positioning and navigation system and its operation method used in this invention are described as follows:

(1) The wavelength of millimeter wave is longer than that of ordinary infrared sensor. When encountering an obstacle, it is relatively easy to bypass, and not easy to be disturbed by the obstacle.

(2) Millimeter wave has a better penetration rate to the tissue due to its longer wavelength; on the contrary, infrared sensor has a relative low penetration rate to the tissue, so it can only use surface feature as a reference point for positioning. In addition, because of the better penetration rate of millimeter wave, it can use the three-dimensional space of the feature object for positioning, or intercept the feature points of different depths for positioning, and the positioning accuracy is obviously better than that of the infrared sensor.

(3) The positioning accuracy of infrared sensor is easily affected by interference. Because the natural radiation of human body and the thermal radiation emitted by mechanical equipment have a frequency band within the infrared band, the thermal radiation will interfere with the accuracy of infrared sensing. However, the millimeter wave will not be interfered by the thermal radiation. In addition, due to the widespread use of infrared related devices, they are easy to interfere with each other. Especially in the operation, many instruments may be operated at the same time, which may interfere with infrared navigation and positioning. Finally, because the atmosphere has a better penetration rate of infrared, the infrared radiation outside the operation environment may have an impact on positioning and navigation. Moreover, the penetration rate of the atmosphere to millimeter wave is extremely relatively low, so the millimeter wave interference by the external environment can be neglected.

(4) Tissue identification: because different tissues have different penetration rate and absorptivity of electromagnetic wave, it can realize that the signal is coming from which tissue by analyzing the signal reflected back and forth by millimeter wave.

As the fact understood by a person skilled in the art, the foregoing preferred embodiments of the present invention are illustrated of the present invention rather than limiting of the present invention. It is intended to cover various modifications and similar arrangements included within the spirit and scope of the appended claims, the scope of which should be accorded the broadest interpretation so as to encompass all such modifications and similar structure. While the preferred embodiment of the invention has been illustrated and described, it will be appreciated that various changes can be made therein without departing from the spirit and scope of the invention.

What is claimed is:

1. A positioning and navigation system for surgery, comprising: a wearable device including at least one processor, at least one millimeter-wave positioning module coupled to said at least one processor, and a first display module coupled to said at least one processor, a surgical navigation module coupled to said at least one processor, and a surgical navigation information based on a three-dimensional overlapped image inputted into said surgical navigation module; and a surgical instrument coupled to said wearable device;

wherein said at least one millimeter-wave positioning module further includes a signal processing unit, a signal transmitting unit and a signal receiving unit, wherein said signal processing unit is coupled to said signal transmitting unit and said signal receiving unit;

wherein said signal processing unit calculates relative distance between said millimeter wave positioning module and said surgical site of said patient based on time difference from a millimeter wave transmitting signal of said signal transmitting unit to a millimeter wave receiving signal of said signal receiving unit;

wherein said at least one processor receives a local three-dimensional feature points image constructed by the millimeter-wave positioning module in real time;

wherein said at least one millimeter-wave positioning module is configured to obtain said local three-dimensional feature points image and at least one first sensing information;

wherein said at least one processor overlapping said surgical navigation information with a local three-dimension feature points image to display said surgical path and dangerous areas on said first display module in real time;

wherein said wearable device further comprises an auxiliary positioning module coupled to said at least one processor, and said auxiliary positioning module obtains at least one second sensing information wherein said at least one first sensing information and said at least one second sensing information include moving position, acceleration, angular velocity, rotation angle or a combination thereof of said wearable device.

2. The system of claim 1, wherein said at least one processor includes a first information transceiver module receiving at least one image information scanned by an external device, and a first image processing module coupled to said first information transceiver module.

3. The system of claim 2, wherein said first image processing module is configured to reconstruct said at least one image information to form a three-dimensional virtual image.

4. The system of claim 3, wherein said first image processing module receives a global three-dimensional feature points image and overlaps said three-dimensional virtual image with said local three-dimensional feature points image to form an overlapped three-dimensional image displaying on said first display module.

5. The system of claim 1, wherein said auxiliary positioning module comprises at least one sensing unit, at least one camera unit or the combination thereof.

6. The system of claim 1, wherein said first image processing module is configured to correct and update said overlapped three-dimensional image in real time through said first sensing information and said second sensing information.

7. The system of claim 2, further comprising an external server coupled to said wearable device wherein said external server includes:

a second information transceiver module receiving said at least one image information scanned by said external device;

a second image processing module coupled to said at least one millimeter-wave positioning module and said second information transceiver module; and a second display module coupled to said second image processing module.

8. A positioning and navigation system for surgery, comprising:

a wearable device including at least one processor, an auxiliary positioning module to detect a surgical site of a patient, wherein said auxiliary positioning module comprises at least one sensing unit, and a first display module coupled to said at least one processor, a surgical navigation module coupled to said at least one processor, and a surgical navigation information based on a three-dimensional overlapped image inputted into said surgical navigation module;

wherein said auxiliary positioning module is configured to obtain at least one sensing information includes moving position, acceleration, angular velocity, rotation angle or a combination thereof of said wearable device;

at least one millimeter-wave positioning module coupled to said at least one processor; and a surgical instrument coupled to said wearable device and said at least one millimeter-wave positioning module;

wherein said at least one millimeter-wave positioning module further includes a signal processing unit, a signal transmitting unit and a signal receiving unit, wherein said signal processing unit is coupled to said signal transmitting unit and said signal receiving unit;

wherein said signal processing unit calculates relative distance between said millimeter wave positioning module and said surgical site of said patient based on time difference from a millimeter wave transmitting signal of said signal transmitting unit to a millimeter wave receiving signal of said signal receiving unit;

wherein said at least one processor receives a local three-dimensional feature points image constructed by the millimeter-wave positioning module in real time;

wherein said at least one processor overlapping said surgical navigation information with a local three-dimension feature points image to display said surgical path and dangerous areas on said first display module in real time.

9. The system of claim 8, wherein said at least one processor includes a first information transceiver module receiving at least one image information scanned by an external device and a first image processing module coupled to said first information transceiver module and said at least one millimeter-wave positioning module.

10. The system of claim 9, wherein said first image processing module is configured to reconstruct said at least one image information to form a three-dimensional virtual image.

11. The system of claim 10, wherein said auxiliary positioning module is configured to obtain at least one sensing information and at least one two-dimensional image, and said at least one millimeter-wave positioning module is configured to obtain a depth information.

12. The system of claim 10, wherein said first image processing module is configured to reconstruct said at least one sensing information and said at least one two-dimensional image to form the local three-dimensional feature points image.

13. The system of claim 12, wherein said first image processing module is configured to overlap said three-dimensional virtual image and said local three-dimensional feature points image to form an overlapped three-dimensional image for displaying on said first display module.

14. The system of claim 13, wherein said first image processing module is configured to correct and update said overlapped three-dimensional image in real time through said at least one sensing information.

15. The system of claim 9, further comprising an external server coupled to said wearable device wherein said external server includes:
- a second information transceiver module receiving said at least one image information scanned by said external device;
- a second image processing module coupled to said auxiliary positioning module and said at least one millimeter-wave positioning module; and
- a second display module coupled to said second image processing module.

16. An operation method of a positioning and navigation system for surgery, comprising:
- (A) detecting a surgical site of a patient to obtain a local three-dimensional feature points image by a wearable display device, wherein said wearable display device includes at least one millimeter-wave positioning module, an auxiliary positioning module, a surgical navigation module, and a display module;
- wherein a surgical navigation information based on a three-dimensional overlapped image is inputted into said surgical navigation module;
- (B) overlapping a three-dimensional virtual image with said local three-dimensional feature points image to form an overlapped three-dimensional image to display on said first display module; and
- (C) performing a surgical procedure for said patient according to said overlapped three-dimensional image;
- wherein said wearable display device is correcting and updating said overlapped three-dimensional image through at least one sensing information detected by said auxiliary positioning module or said millimeter wave positioning module;
- wherein said at least one millimeter-wave positioning module further includes a signal processing unit, a signal transmitting unit and a signal receiving unit, wherein said signal processing unit is coupled to said signal transmitting unit and said signal receiving unit;
- wherein said signal processing unit calculates relative distance between said millimeter wave positioning module and said surgical site of said patient based on time difference from a millimeter wave transmitting signal of said signal transmitting unit to a millimeter wave receiving signal of said signal receiving unit;
- wherein said surgical navigation information overlapping with a local three-dimension feature points image to display said surgical path and said dangerous areas on said first display module in real time.

17. The method of claim 16, wherein prior to said step (A), further comprising the following steps: (a) scanning said surgical site of said patient to obtain at least one first two-dimensional image by an external device; and
- (b) reconstructing said at least one two-dimensional image to form said three-dimensional virtual image by said first image processing module.

* * * * *